(12) United States Patent
Houston

(10) Patent No.: US 7,212,639 B1
(45) Date of Patent: May 1, 2007

(54) ELECTRO-LARYNX

(75) Inventor: Kenneth M. Houston, Acton, MA (US)

(73) Assignee: The Charles Stark Draper Laboratory, Cambridge, MA (US)

( * ) Notice: Subject to any disclaimer, the term of this patent is extended or adjusted under 35 U.S.C. 154(b) by 0 days.

(21) Appl. No.: 09/475,390

(22) Filed: Dec. 30, 1999

(51) Int. Cl.
G05B 11/32 (2006.01)

(52) U.S. Cl. ...................................... 381/70

(58) Field of Classification Search ............... 381/70, 381/151, 326, 380, 396; 623/9; 704/266, 704/258, 278, 261; 181/126, 128, 181, 726; 697/56–57; 128/207.14; 84/375
See application file for complete search history.

(56) References Cited

U.S. PATENT DOCUMENTS

| | | | | |
|---|---|---|---|---|
| 3,925,616 A | * | 12/1975 | Sondhi | 704/201 |
| 3,978,286 A | * | 8/1976 | Watson | 381/70 |
| 4,039,756 A | * | 8/1977 | Burtschi | 381/70 |
| 4,264,989 A | | 5/1981 | Wiley | 623/9 |
| 4,292,472 A | | 9/1981 | Lennox | 381/70 |

(Continued)

FOREIGN PATENT DOCUMENTS

| | | | |
|---|---|---|---|
| WO | WO 99/53867 | * | 10/1999 |

OTHER PUBLICATIONS

Kenneth, Development of Sound Source Components for a New Electrolarynx Speech Prosthesis Sep. 1998, The charles Stark Draper Laboratory, Inc.*

Primary Examiner—Vivian Chin
Assistant Examiner—Lun-See Lao

(74) Attorney, Agent, or Firm—Mark G. Lappin; Foley & Lardner LLP

(57) ABSTRACT

An improved electro-larynx includes a linear transducer and/or an improved waveform generator. The improved electro-larynx sets up a sound wave within the pharynx of the user which closely approximates a normal glottal excitation. The linear transducer preserves the harmonic structure of a glottal source wave generated by the waveform generator and translates it into a vibration. The transducer includes an armature assembly, suspension assembly, and coupler disk coupled together to move in concert. The armature assembly vibrates as a function of the desired and input glottal source wave, which in turn causes an immediate and corresponding vibration of the coupler disk. The suspension assembly constrains armature movement to one dimension and provides additional compliance. The coupler disk includes a substantially flat surface suitable for engaging the surface of a user's throat and vibrates as a linear function of the input glottal source wave. The improved waveform generator produces a relatively good approximation of an actual glottal source waveform by preferably deriving it from actual voice data and having the effects of the modulation of the vocal tract removed. As a result, the harmonic structure of the glottal source waveform has overtones which drift in frequency, similar to normal glottal excitations. The waveform generator also allows user adjustment of the pitch and amplitude of the glottal source wave and smoothes out any distortions caused by the process of obtaining the glottal data used to generate the glottal source wave. The waveform generator bolsters the frequency response at the high end of the spectrum to compensate for any roll-off, yielding a frequency response spectrum of about 20–5 Khz. The responsiveness of the linear transducer allows the glottal source wave's pitch, amplitude, and harmonic structure to be communicated through the coupler disk and realistic glottal source waves to be transduced into the user's pharynx, resulting in the production of substantially normal speech.

25 Claims, 13 Drawing Sheets

U.S. PATENT DOCUMENTS

| | | | |
|---|---|---|---|
| 4,338,488 A | 7/1982 | Lennox | 381/70 |
| 4,401,850 A * | 8/1983 | Harbeson | 704/207 |
| 4,473,905 A | 9/1984 | Katz et al. | 381/70 |
| 4,502,150 A | 2/1985 | Katz et al. | 381/70 |
| 4,550,427 A | 10/1985 | Katz et al. | 381/70 |
| 4,586,931 A | 5/1986 | Blom et al. | 623/9 |
| 4,672,673 A | 6/1987 | Katz et al. | 381/70 |
| 4,797,926 A * | 1/1989 | Bronson et al. | 704/214 |
| 4,821,326 A * | 4/1989 | MacLeod | 704/261 |
| 5,128,905 A * | 7/1992 | Arnott | 367/140 |
| 5,171,930 A * | 12/1992 | Teaney | 84/725 |
| 5,326,349 A | 7/1994 | Baraff | 623/9 |
| 5,400,434 A * | 3/1995 | Pearson | 704/264 |
| 5,792,073 A * | 8/1998 | Keefe | 600/559 |
| 5,812,681 A | 9/1998 | Griffin | 381/70 |
| 6,252,966 B1 * | 6/2001 | Griffin | 381/70 |
| 6,359,988 B1 * | 3/2002 | Espy-Wilson | 381/70 |

* cited by examiner

30

FIGURE 5A
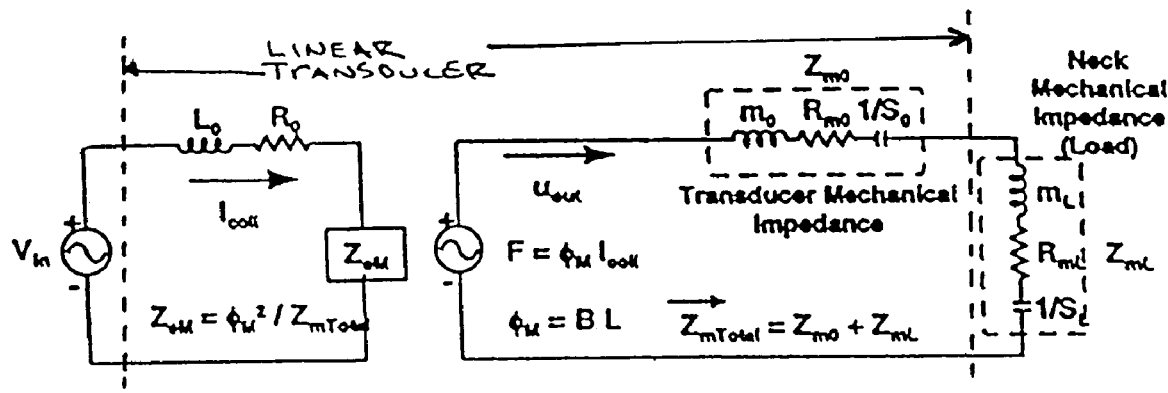
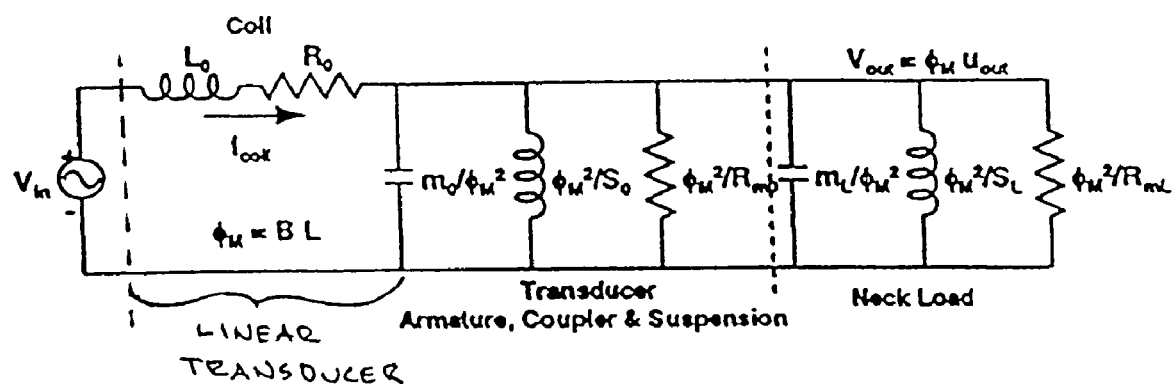
FIGURE 5B

FIGURE 7A
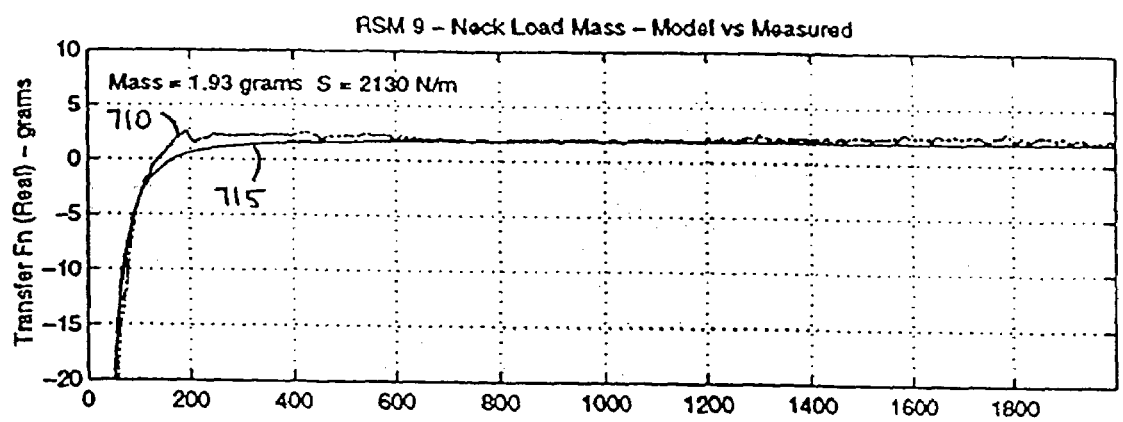
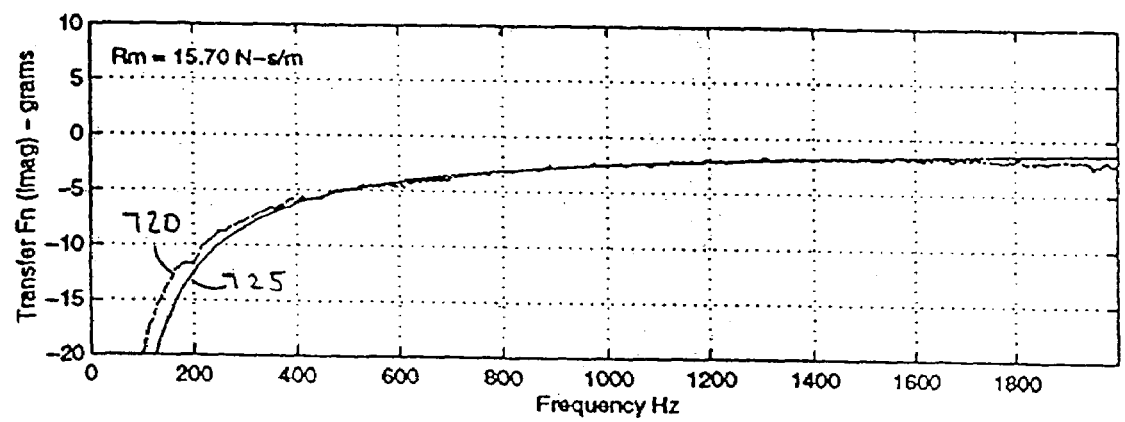
FIGURE 7B

ELECTRO-LARYNX

FIELD OF THE INVENTION

The present invention relates to devices used to facilitate speech in those individuals without vocal cords.

BACKGROUND OF THE INVENTION

Every year in the United States alone, thousands of people lose their vocal cords because of laryngeal cancer or trauma. For many of these people (i.e., laryngectomees), the only option for regaining a speech capability is through the use of an electro-larynx (E-L), which is a handheld battery-operated shaker or vibrator that is pressed against a predetermined area of the throat to produce a speech-like sound and pattern. The electro-larynxes of the prior art are devices having non-linear transducers which produce speech that is very machine-like in sound, with low levels of loudness and intelligibility. This relatively poor speech sound quality often draws undesired attention to the user and can result in strained, unnatural communication with others.

FIG. 1A shows a partial cross sectional profile view of a human 10 with a normally structured larynx 12, including vocal cords 14, and vocal tract 16. The vocal tract 16 includes the pharynx, tongue, mouth and lips of the person. To form speech, air is forced through the larynx by the lungs and simultaneously, in response to signals from the laryngeal nerve (not shown), the vocal cords 14 are selectively tensioned so that the airflow causes the vocal cord to vibrate to create sound waves, referred to as glottal source waves and their form is referred to as a "glottal source waveform". The glottal source waves are modulated by the vocal tract to form speech emitted from the mouth, as depicted by arrows 18. In the case of a laryngectomee, shown in FIG. 1B, air is drawn into the lungs (not shown) via an opening 32 in the trachea 34, as depicted by arrows 38a. Air is then forced out of the lungs and exits opening 32 in trachea 34, as depicted by arrows 38b. Therefore, the air flow never passes through the vocal cords (which have been removed) or the vocal tract 36. Consequently, the airflow from the lungs cannot create glottal source waves and the vocal tract remains idle with regard to the creation of speech.

The possibilities for creating speech without the assistance of an electro-larynx or similar device are few and are commonly considered inadequate. For example, one such process for creating speech without an electro-larynx is called "esophageal speech". According to this process, a person swallows air (that is, draws air through the mouth into the esophagus), and then regurgitates it through the vocal tract for modulation. This process produces poor quality speech and is generally cumbersome and embarrassing.

Assisted speech using an electro-larynx is typically preferred over the above methods for producing speech by laryngectomees. In FIG. 1C, a person 50 is shown using a prior art electro-larynx 100. Electro-larynx 100 is pressed against an area of the throat 54 and produces sound waves which are propagated through the tissue of the throat to the vocal tract 56. The waveform entering the vocal tract is an approximation of a glottal source waveform. Vocal tract 56 then modulates the received waveform to form speech, depicted by arrow 58, much the way the vocal tract would modulate glottal source waves supplied by the vocal cords, if they were present.

A partial diagrammatic view of prior art electro-larynx 100 is shown in FIG. 2. The prior art electro-larynx includes a non-linear transducer 210, a power amplifier 250, and a waveform generator 260. The transducer and waveform generator are the heart of the electro-larynx 100 and predominantly dictate the quality of speech that can be produced using the electro-larynx 100. The waveform generator produces a base waveform at the desired fundamental frequency (typically through use of pulsed waveforms), and the power amplifier provides a high output current that drives the transducer. The transducer converts electrical energy into sound waves. Ideally, the waveform output from the tissue against which the electro-larynx is pressed and delivered to the vocal tract, is identical to the glottal source waveform that would be produced by the vocal cords and delivered to the vocal tract. However, due to limitations in prior art non-linear transducers and electro-larynx waveform generators, only rough approximations of the glottal source waveform are possible.

The physical make up and mechanical characteristics of non-linear transducers used in conventional electro-larynxes compromise the output signal of the electro-larynx. For example, one significant limitation of such an electro-larynx is that there is little control over the achievable speech quality due to the non-linear nature of the transducer. Only the fundamental frequency is controlled by the waveform generator; the spectrum of the resulting sound (reflecting more of the harmonics than the fundamental frequency) is a complex function of the mechanical structure of the transducer, and is not controlled. Furthermore, the mechanical characteristics of the non-linear transducer add spectral limitations to the electro-larynx that often results in a low frequency deficit below approximately 500 Hz, which makes certain vowels hard to distinguish.

The illustrated prior art non-linear transducer 210 of FIG. 2 is generally cylindrical, extending along a principal axis-X. A motor assembly 220 is made of a combination of steel and magnetic materials, typically layered, that form a cylindrical void region extending along the X axis, within which a strong radial magnetic field is created. An armature assembly 224 is disposed within the cylindrical gap and consists of a wire voice coil 212 that is wrapped around a bobbin 214, which is attached to an axially-extending rigid striker 218. Bobbin 214 is supported to permit vibratory axial motion (along the X-axis) by a suspension assembly 216. A coupler disk 222 is dispensed at one end of housing 220, within striking range of striker 218. By appropriate application of electrical current to voice coil 212, operating within the magnetic field of motor housing 220, bobbin 214 is caused to axially pulsate. As a result, the armature assembly 224 vibrates periodically at a pitch frequency, which is a function of the current applied to wire 212 and the mechanical characteristics of the transducer components. As armature assembly 224 (supported by suspension assembly 216) vibrates, striker 218 strikes coupler disk 222 and the coupler disk vibrates in response to being struck. As shown in FIG. 2, an external surface A of coupler disk 222 is pressed against the user's throat. As coupler disk 222 vibrates, it couples its vibratory motion to the throat, which in-turn creates acoustic waves at the base of the vocal tract. As modulated by the vocal tract, these acoustic waves emerge as speech from the lips of the user.

The striking action of the armature striker against the coupler disk creates sound with a pressure waveform in the form of an impulse train. The spectrum of this pressure waveform is a function of the mechanical properties of the coupler disk and its mounting to the electro-larynx housing. The coupler-striker interaction is more efficient at producing high frequency sound than it is at producing low frequency sound. Thus, the output spectrum of an electro-larynx having a non-linear transducer is inherently more narrow than the spectrum needed to create natural sounding speech. Also, a relatively high level of noise is generated by the transducer due to the striking of the armature against the coupler disk. This noise becomes constant interference to the desired signal by filling in spectral and temporal valleys where sound should be absent.

Waveform generators typically used in electro-larynxes are inherently limited. For example, a typical electro-larynx waveform generator produces a simple periodic (e.g., sinusoid) waveform having a single fundamental frequency. Such a system produces unnatural, monotone speech due to the simplified waveform and the non-linear nature of the transducer. Often such an electro-larynx includes an embedded control (e.g., potentiometer) with which a user may select a fundamental frequency, within a certain predetermined range of frequencies. However, monotone speech is always produced when the electro-larynx is in use.

In another electro-larynx, the frequency is user variable during operation, within a predetermined range, but the waveform is still of a simple shape. In such a case, the frequency is controlled by a pressure sensitive finger control, wherein a change in the pressure exerted on the finger control produces a corresponding change in the frequency of the output wave (and resulting speech). While this ability to change the frequency during operation is useful, it is substantially impossible for a user to produce a wave having the irregular harmonic characteristics needed to approximate that of normal human speech, and the sound quality is still highly machine-like and mechanical.

Accordingly, it is an object of the present invention to provide an electro-larynx system which delivers an improved glottal source waveform to the vocal tract of a user to produce improved, more natural sounding speech.

SUMMARY OF THE INVENTION

The invention is an improved electro-larynx, i.e., a preferably handheld device used to assist laryngectomees in the production of speech. Among other things, the improved electro-larynx includes a linear transducer and/or an improved waveform generator. The electro-larynx is capable of setting up a glottal source sound wave within the pharynx of a user which closely resembles a normal glottal excitation. The improved waveform generator produces a relatively good approximation of a glottal source waveform, having a harmonic structure substantially similar to that of natural human speech. For the most part, the linear transducer preserves this harmonic structure by producing an output vibration which is a substantially linear function of the waveform produced by the waveform generator. This combination results in an electro-larynx that facilitates the production of substantially natural sounding speech by the user. Preferably, the wave produced by the waveform generator is delivered to a linear power amplifier and from there to the transducer, which preserves its form and outputs it to the neck of a user in the form of the output vibration. In some forms, these components, along with a battery power source, are encased in a housing formed to facilitate protection of the interior components of the electro-larynx and manipulation of the electro-larynx by a user.

The linear transducer includes a motor assembly, an armature assembly, a suspension assembly, and a coupler disk. The motor assembly preferably includes a combination of steel and magnetic materials layered together to form a rigid cylindrical housing having a cupped portion at one end. The motor assembly is formed about a central T axis and a circular opening is formed in the cupped portion, concentric with the motor assembly, to accommodate and circumscribe the coupler disk. A central void region is formed within the motor assembly, which has a strong magnetic field. The armature assembly is coupled to the coupler disk and supported substantially within the central void region of the motor assembly moveably supported by the suspension assembly. The suspension assembly constrains the armature assembly to motion in one dimension, along the T axis. In a simple form, the suspension assembly may be a spring and pin assembly or it may be a flexible, planar membrane made from a material such as rubber. The coupler disk is made from a rigid material and has an external, substantially flat surface which is selectively placed against the throat of a user to facilitate the translation of the electro-larynx output vibration into a glottal-like sound excitation in the user's throat or pharynx.

In the preferred form, the armature assembly includes a bobbin that is maintained within the central void region magnetic field of the motor assembly. A voice coil wire is wrapped around the bobbin and is electrically connected to the power amplifier. The waveform generator delivers a waveform to the power amplifier and the amplifier boosts the amplitude of the waveform and delivers it to the voice coil wire in the form of an electrical signal of a certain voltage, current, and harmonic structure. When the current is applied through the coil (within the magnetic field) a corresponding vibration of the bobbin (and armature assembly) occurs. Because the coupler disk and armature assembly are rigidly coupled together, and supported by the suspension assembly, the resulting vibration of the armature assembly is directly and immediately transferred to the coupler disk, according to a substantially linear relationship. The mass, compliance, and resistance of the armature assembly and its mount to the housing, along with the mechanical impedance of the throat, determine the overall frequency response of the electro-larynx. These values are determined and the transducer is designed to provide a frequency response which is substantially flat over a frequency range of about 20–2000 Hz.

To obtain a rich, natural sound, a proper harmonic structure is required where the overtones of the glottal excitation waveform drift in frequency, rather than being in lock-step, relative to the fundamental. Therefore, the waveform generator may include glottal sample data, derived from actual voice data. The glottal sample data is approximately periodic, and embodies the harmonic structure of the original voice data. The effects of the vocal tract are removed from the original voice data to arrive at data which corresponds to the glottal excitation typically produced by the vocal cords (i.e., pre-vocal tract), rather than the post-vocal tract modulated speech which exits the lips. This pre-vocal tract waveform is then modulated by user's vocal tract to accomplish natural sounding speech. In another embodiment, the waveform generator may be model-based, wherein it includes models, preferably rule-based, of typical glottal source waveforms, including relationships between amplitudes and harmonics.

The waveform generator includes a pitch adjuster and an amplitude adjuster to allow for variations in these parameters which improve the quality of the speech. In a preferred form the electro-larynx includes external user controls to accomplish such variations when desired. In another form, inputs for such controls could be obtained by biofeedback. An equalization filter takes the glottal sample wave data, with adjusted pitch and/or amplitude if desired, and smoothes out any distortions introduced by the transfer function or process used to obtain the glottal sample data. Additionally, the equalization filter compensates for any roll-off of the high end of the frequency spectrum of the electro-larynx output, e.g. above about 1 KHz.

In accordance with the present invention, the linear transducer has an output coupler vibration velocity that is proportional (i.e., linear) to the input voltage or current of the shaker. Also, the output wave shape corresponding to the vibration of the coupler replicates the input voltage wave shape over the bandwidth of the device. Because the coupler disk is directly connected to the armature assembly (possibly via a suspension assembly), any movement of the armature assembly results in a corresponding movement of the neck tissue. This direct coupling of the coupler disk and armature assembly (supported by the suspension assembly), obviates the need for the striking of the armature against a coupler disk. The linearity of the transducer allows for a high degree of preservation of the attributes of the input waveform resulting speech, such as spectral shape, and the capacity for low-frequency motion of the coupler disk avoids a deficit in spectral content at low-frequencies. The purely electronic waveform synthesis of the waveform generator allows for rapid responses to control inputs (such as pitch and amplitude), permits adjustment of the spectrum as desired, and enables inclusion of features which improve the naturalness of the resulting sound. In particular, the harmonic structure of the output can be controlled so as to avoid a metallic or machine-like sound quality.

BRIEF DESCRIPTION OF THE DRAWINGS

The foregoing and other objects of this invention, the various features thereof, as well as the invention itself, may be more fully understood from the following description, when read together with the accompanying drawings, described:

FIGS. 5A and 5B are equivalent circuit diagrams of the linear transducers of FIGS. 4A and 4B.

FIGS. 7A and 7B are representative plots of real and imaginary parts of neck mass load values over the desired audio frequency range, determined by the load measurement system of FIG. 6.

For the most part, and as will be apparent when referring to the figures, when an item is used unchanged in more than one figure, it is identified by the same alphanumeric reference indicator in all figures.

DETAILED DESCRIPTION OF THE PREFERRED EMBODIMENTS

The present invention is an improved electro-larynx having a substantially linear transducer and/or an improved waveform generator. The improved electro-larynx is capable of setting up a sound wave in the pharynx of a user which closely resembles a normal glottal excitation. The waveform generator produces a relatively good synthesized approximation of a glottal source waveform, having a harmonic structure substantially similar to that of normal human speech. The linear transducer is highly responsive and preserves this harmonic structure by producing an output vibration which is a substantially linear function of the glottal source waveform produced by the waveform generator. The waveform generator may use glottal sample data preferably derived from actual voice data to form the wave sent to the transducer, such data having the effects of the vocal tract modulation compensated out. Consequently, the post transduction sound waves to be modulated by the vocal tract of the user are similar in frequency, amplitude, and spectral content to those sound waves normally produced by the vocal cords. Accordingly, the waveform set up in the pharynx and modulated by the vocal tract results in the production of natural sounding speech.

Figure 3:
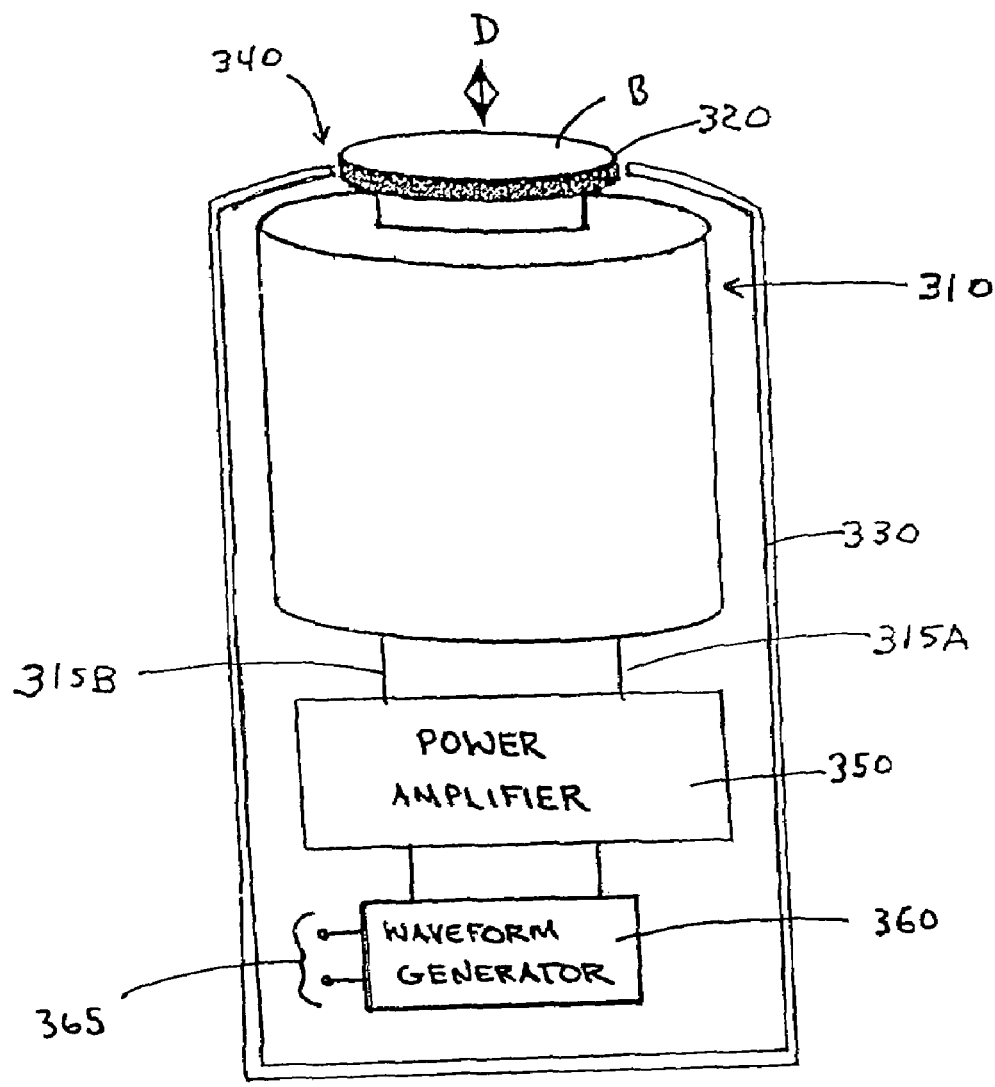
FIG. 3 is a diagrammatic view of an electro-larynx in accordance with the present invention.

A handheld electro-larynx 300 in accordance with the present invention is shown in FIG. 3. Electro-larynx 300 includes a linear transducer 310, power amplifier 350, waveform generator 360 and power source (not shown), all encased within a handheld case 330. The power source is preferably a battery. Handheld case 330 is suitable for gripping and holding during operation by a user of the device (i.e., a laryngectomee). Case 330 may be made from any of a variety of materials, such as molded plastic or thin light-weight formed metal. The case is generally cylindrical and has an opening 340 defined in a top end thereof. The linear transducer is encased by and secured within case 330, with the exception of a coupler disk 320. The coupler disk has an engagement surface B exposed through opening 340 to facilitate direct physical contact with a predetermined area of a user's throat. The vibration of coupler disk 320, in the direction of arrow D, is transferred to the throat of the user when the electro-larynx is pressed against the user's throat. As a result, a corresponding wave is transduced into the pharynx of the user.

Figure 4A:
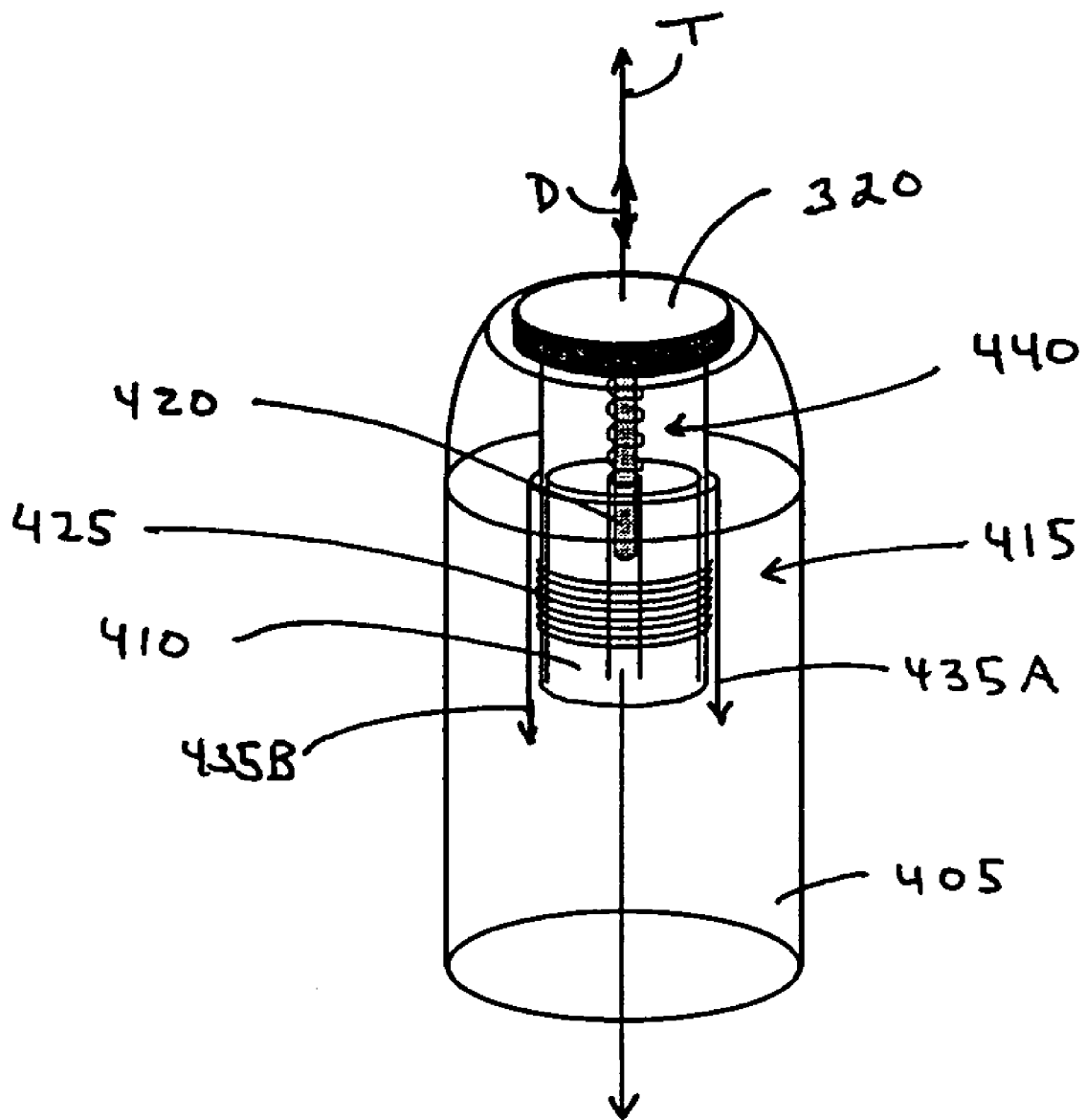
FIGS. 4A and 4B are diagrammatic views of the linear transducer portion of the electro-larynx of FIG. 3 using a spring suspension assembly and a flexible membrane suspension assembly, respectively.
Figure 4B:
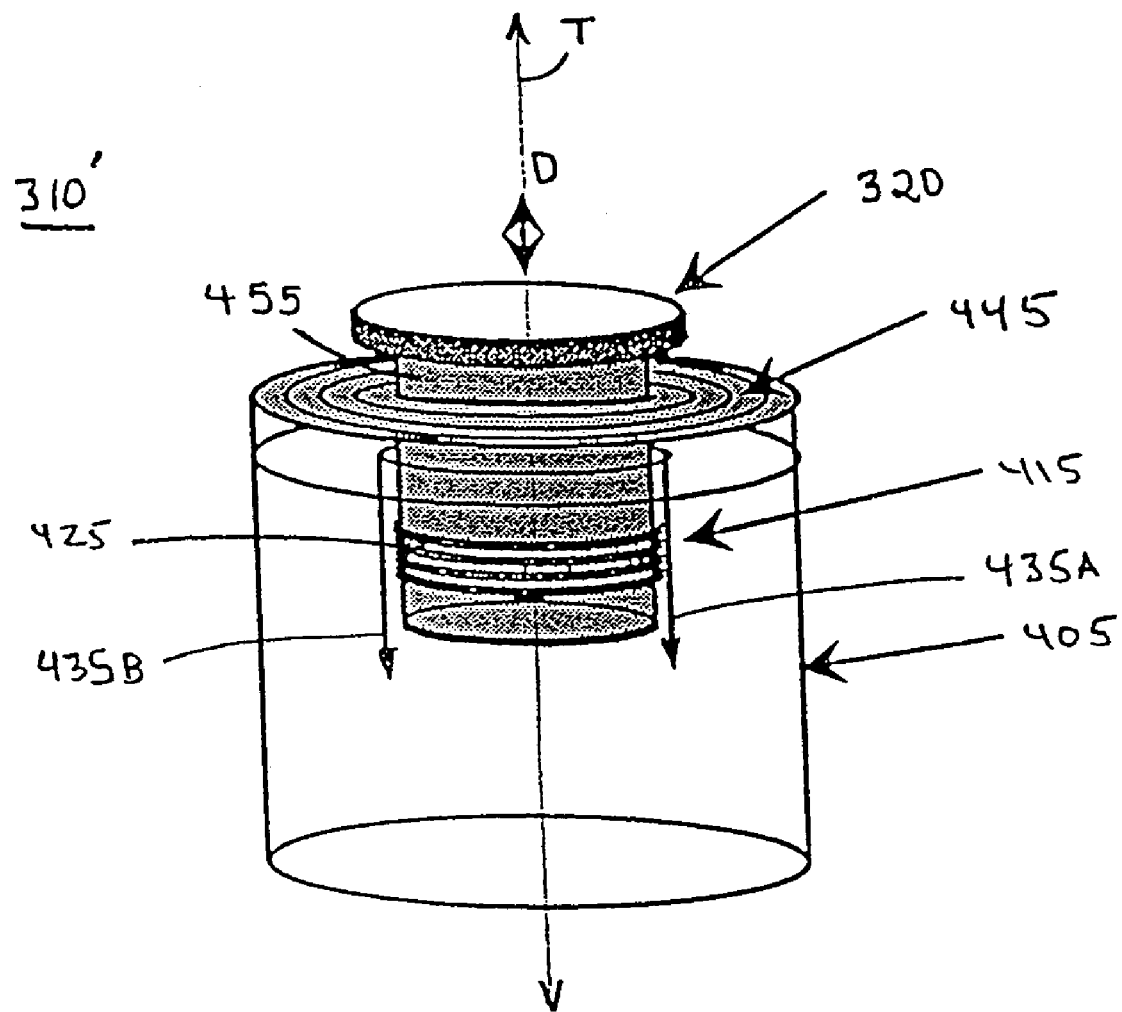

A detailed view of a first embodiment of transducer 310 is shown in FIG. 4A and a second embodiment of transducer 310 is shown in FIG. 4B. In each embodiment, the transducer produces an output vibration of coupler disk 320 in response to, and as a linear function of, an input signal. In the preferred form, the transducer is an electro-magnetic apparatus having a substantially cylindrical motor housing 405 centered about a translation axis T and made from magnetic materials such as neodymium, which creates a strong magnetic field within a cylindrical void region formed within housing 220. A generally cylindrical armature assembly 415 is disposed within the void region and is coaxial with magnetic housing 405. Armature assembly 415 includes a voice coil 425 wound around a bobbin 410, such that the voice coil remains within the housing's magnetic field. The armature bobbin is made from a nonmagnetic material such as molded plastic. Voice coil wire 425 includes leads 435A and 435B, which are electrically coupled to leads 315A and 315B (shown in FIG. 3), respectively, of power amplifier 350. When a glottal source waveform having a certain voltage, current, and harmonic structure is delivered to voice coil 425, a corresponding vibration of armature assembly 415 occurs due to its interaction with the magnetic field within housing 405. In other embodiments, rather than the transducer being formed from a magnet and voice coil, the transducer may be formed from a piezo-electric or magneto-restrictive element, as examples. In either case, it is the glottal source waveform output by the waveform generator which substantially serves as the input to and is preserved by the linear transducer 310.

Transducer 310 includes a suspension assembly that translates the vibration of the armature assembly 415 into a substantially linear vibration of coupler disk 320 along the T axis, as depicted by arrow D in FIGS. 4A and 4B. The coupler disk is concentric with the T axis and its engagement surface B is preferably substantially flat (or slightly convex) and lies in a plane that is perpendicular to the T axis. In a first suspension assembly embodiment, shown in FIG. 4A, the suspension assembly is a mechanical spring 440 that is coaxial with the T axis and wrapped around a plastic pin 420, which is also coaxial with the T axis. In this embodiment, the housing 405 includes a top ring 450, which includes a circular opening that is concentric with the T axis. The opening is sufficiently large to allow unabated translation of the pin with respect to the housing. To facilitate such translation of pin 420, the opening may be circumscribed by a ring-shaped grommet, through which pin 420 may freely pass. A first end of pin 420 is fixed to an underside of coupler disk 320 and a second end of pin 420 extends through the opening in top ring 450. Spring 440 extends from top ring 450 to the underside of coupler disk 320 and thereby supports the coupler disk with respect to housing 405. This direct coupling of coupler disk 320 and armature assembly 415, supported by spring 420, provides a linear relationship between the glottal source wave input to the armature assembly leads 435A and 435B and the transducer's vibration output at coupler disk 320.

Figure 1A:
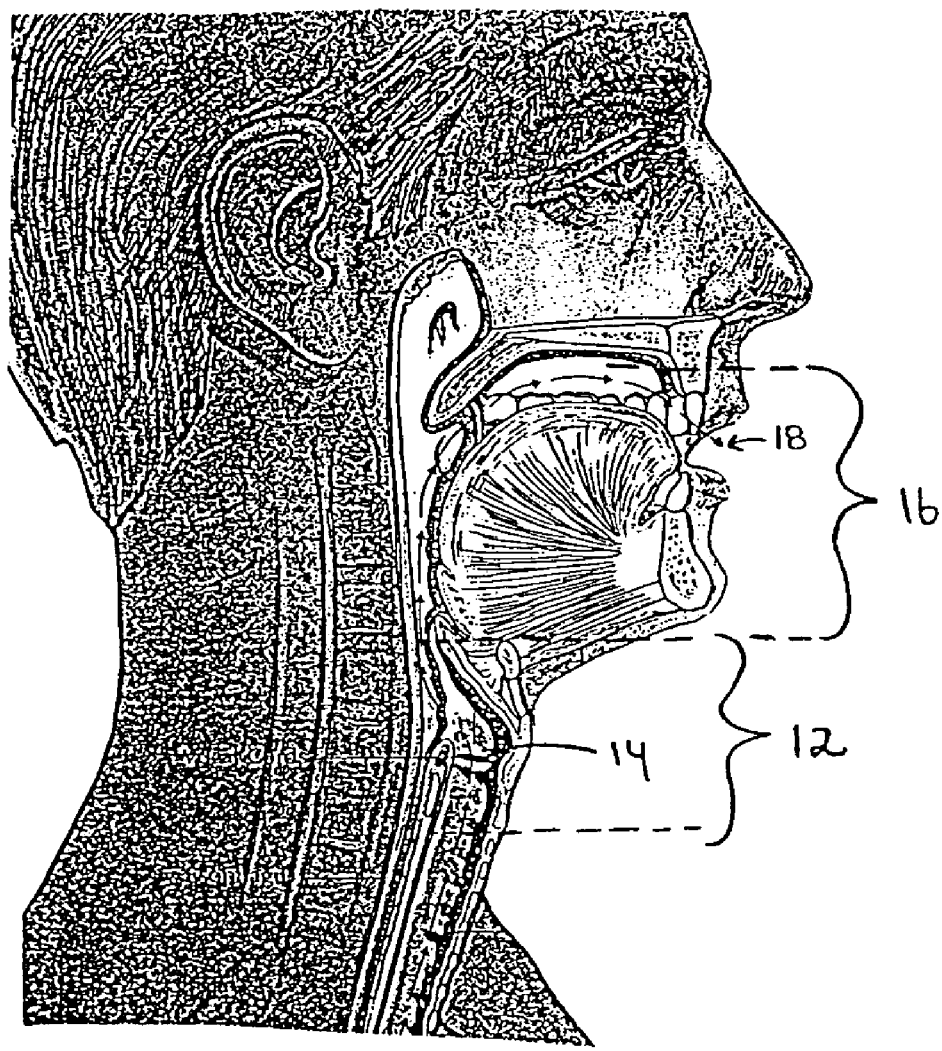
FIG. 1A is a cross-sectional view of a human head and neck with a normally structured larynx and vocal cords.
Figure 1B:
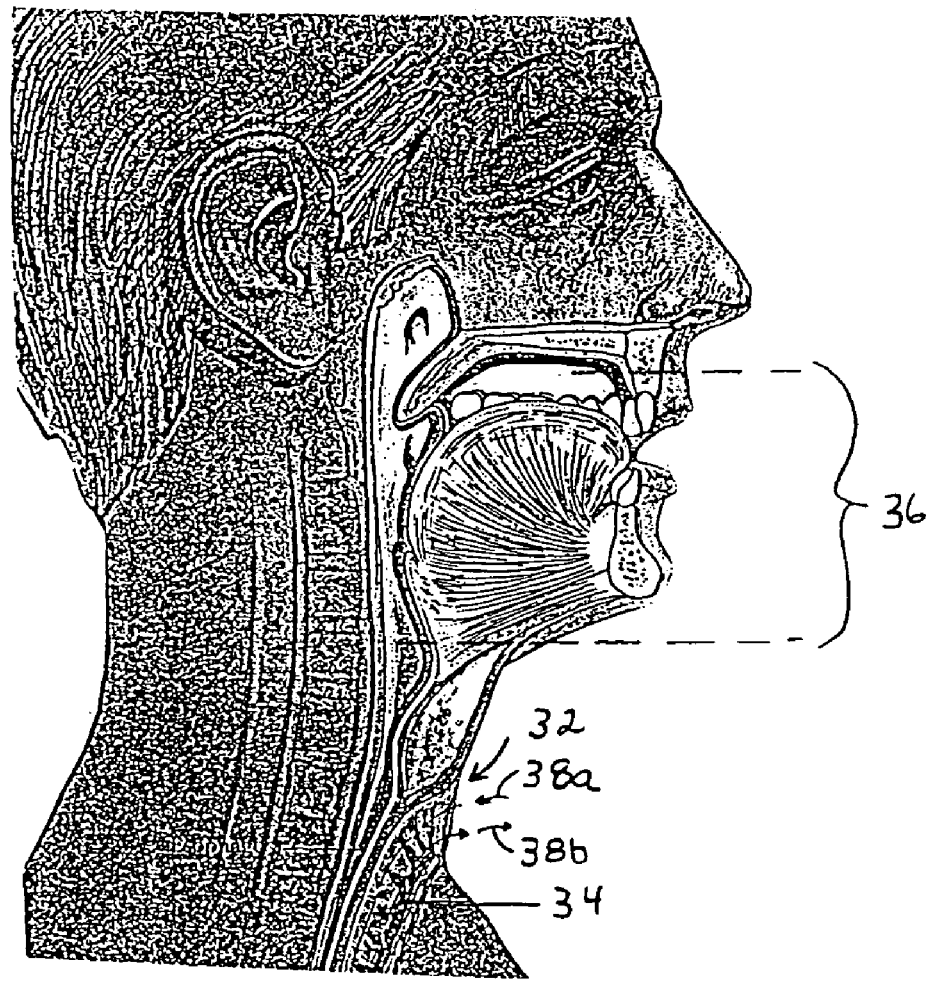
FIG. 1B is a cross-sectional view of a human head and neck with vocal cords removed.
Figure 1C:
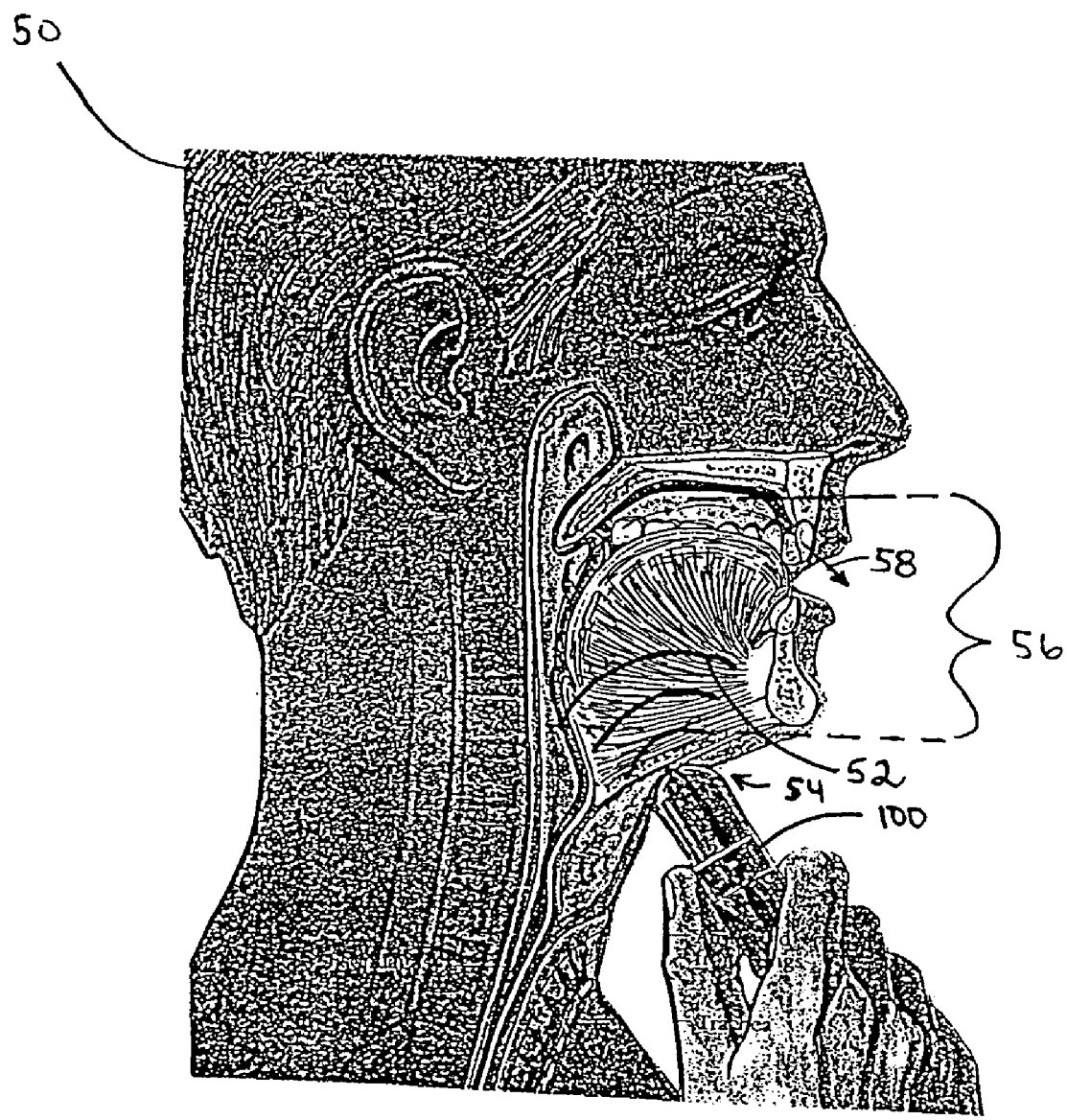
FIG. 1C is a cross-sectional view of the human head and neck and a prior art electro-larynx.
Figure 2:
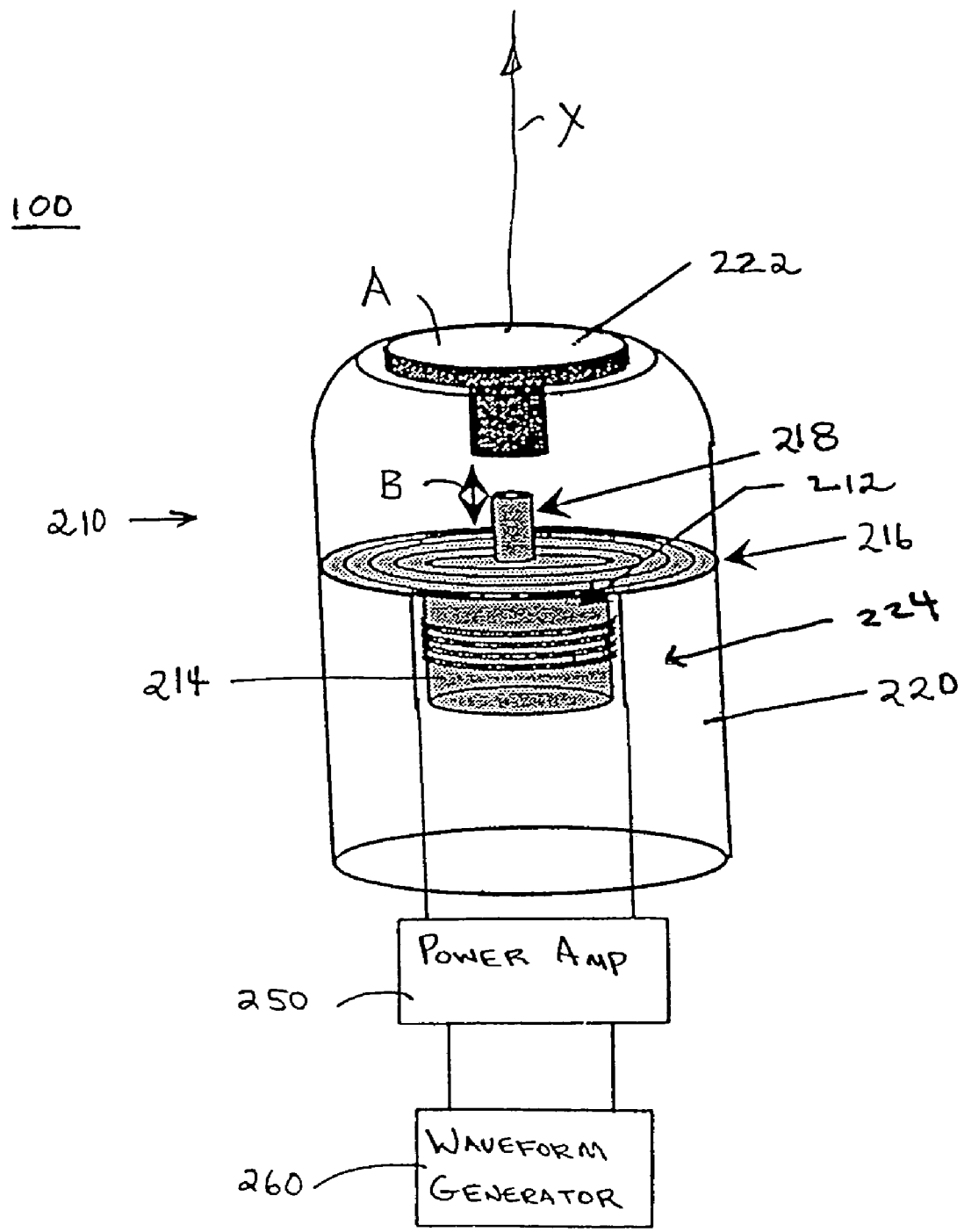
FIG. 2 is perspective diagrammatic view of a prior art non-linear transducer which forms a substantive portion of a prior art electro-larynx.

A second transducer embodiment 310' is shown in FIG. 4B. This embodiment differs from that in FIG. 4A most notably with respect to the suspension assembly. That is, transducer 310' includes a different, i.e., second, suspension assembly embodiment, wherein the suspension assembly is a flexible, planar membrane 445 made from a material such as rubber, and having a first side and a second side and secured across a top opening of cylindrical motor housing 405. The bobbin 410 of armature assembly 415 is coupled to the first (i.e., bottom) surface of membrane 445, accomplishing a mounting of armature assembly 415 to motor housing 405. Due to this direct coupling, the membrane 445 moves coincidentally with the bobbin in the direction of the T axis. Coupler disk 320 is coupled to the second (i.e., top) surface of planar membrane 445 via a coupler mount 455, such that it too experiences a corresponding translation along the T axis in response to movement of armature assembly 415. Alternatively, coupler disk 320 may be coupled directly to armature assembly 415 through the suspension assembly, as well as being coupled to planar membrane 445 for support. In either suspension assembly embodiment, since coupler disk 320 is directly coupled to (or retained by) the suspension assembly and armature assembly, the need for the striking of the coupler disk by a striker (as in FIG. 2) is obviated.

In accordance with well known principles, the mass, compliance, and resistance of the armature assembly and its mount, along with the mechanical impedance of the throat, determine the overall frequency response of the electro-larynx device. FIGS. 5A and 5B show equivalent circuits for modeling the transducers of FIGS. 4A and 4B, which may be represented by the same model. FIG. 5A is a linear transducer electro-mechanical equivalent circuit diagram. The mechanical impedance of the neck serves as the load to the electro-larynx. FIG. 5B is a purely electrical equivalent of the transducer of FIGS. 4A and 4B. The electro-mechanical model defines a "motor" constant $\Phi_M$=BL that translates between electrical and mechanical domains using Force-Voltage/Velocity-Current analogies. The mechanical impedance (i.e., $Z_{mL}$ in FIG. 5A) of the neck represents a load applied to the electro-larynx when in use. An additional load is also caused by acoustic radiation. Ideally, the acoustic radiation results only when the vibrating pharynx wall interacts with the air inside the throat to set up the sound waves, wherein the resulting volume velocity substantially replicates a normal glottal source. However, in reality a relatively small acoustic radiation load is realized. Since it is small relative to the neck impedance, this additional acoustic radiation load can be ignored. Determining the load seen by the electro-larynx allows the frequency response over a desired range to be determined and manipulated, if necessary.

Figure 6:
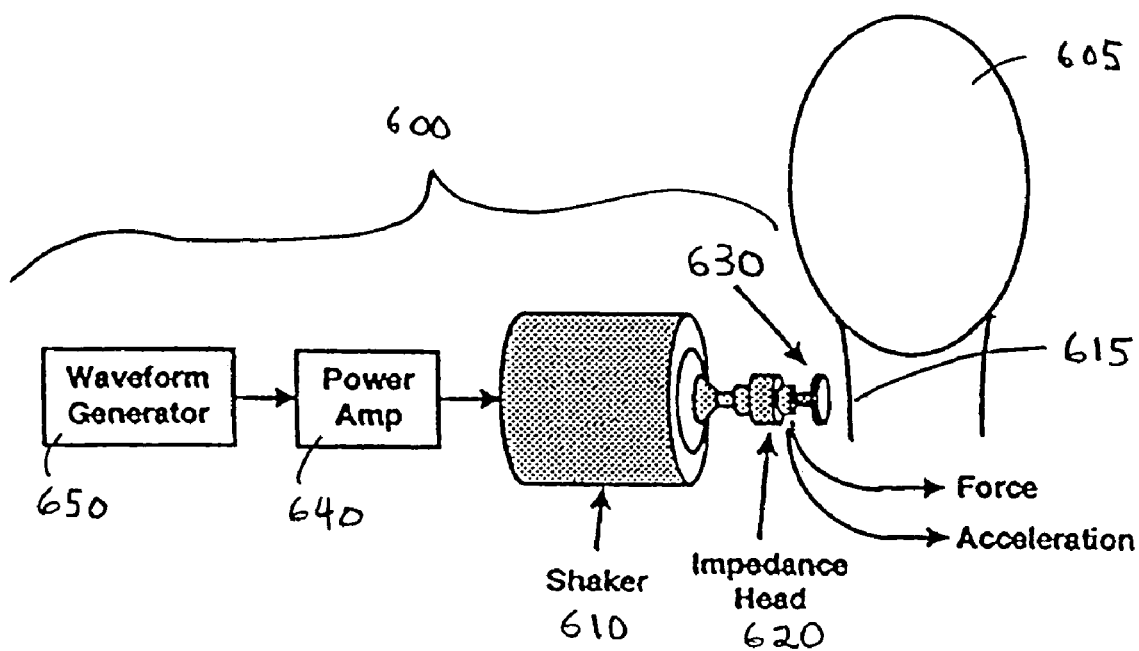
FIG. 6 is a load measurement system for determining neck load impedance values for the equivalent circuits of FIGS. 5A and 5B.

In order to properly specify the mechanical impedance load, so that the transducer can be designed to compensate for the load and deliver a better approximation of the glottal source waveform to the pharynx, measurements of at least one user's neck are taken to facilitate derivation of a representative load value. A system 600 capable of taking such load measurements of a user's 605 neck 615 is shown in FIG. 6. In such a system, an electrodynamic shaker 610 is driven with white noise, generated by waveform generator 650 and propagated by power amplifier 640. The white noise input is transformed into an axial vibration output of a coupler disk 630, which is pressed against throat 615. An impedance head sensor 620 detects and measures the resulting axial force and acceleration to determine the load of the user's neck. Using these measurements, the following transfer function may be used to determine the "apparent mass" $M_L(j\omega)$ for a series Mass-Resistance-Spring combination, and ultimately the mechanical impedance load of the user's neck:

$$M_L(j\omega)=\text{Force/Acceleration}=m_L-S_L/\omega^2-jR_{mL}/\omega,$$

where $m_L$=mass in kg, $R_{mL}$=mechanical resistance in N-s/m (equivalent to kg/sec or "mechanical ohms"), and $S_L$=spring constant in N/m (sometimes specified as the compliance $C_{mL}$=1/$S_L$). The "mechanical impedance" $Z_{mL}(j\omega)$ is the ratio of force to velocity, therefore $$Z_{mL}(j\omega)=\text{Force/Velocity}=j\omega M_L(j\omega)=R_{mL}+j(\omega m_L-S/\omega)-s/m.$$

Figure 8:
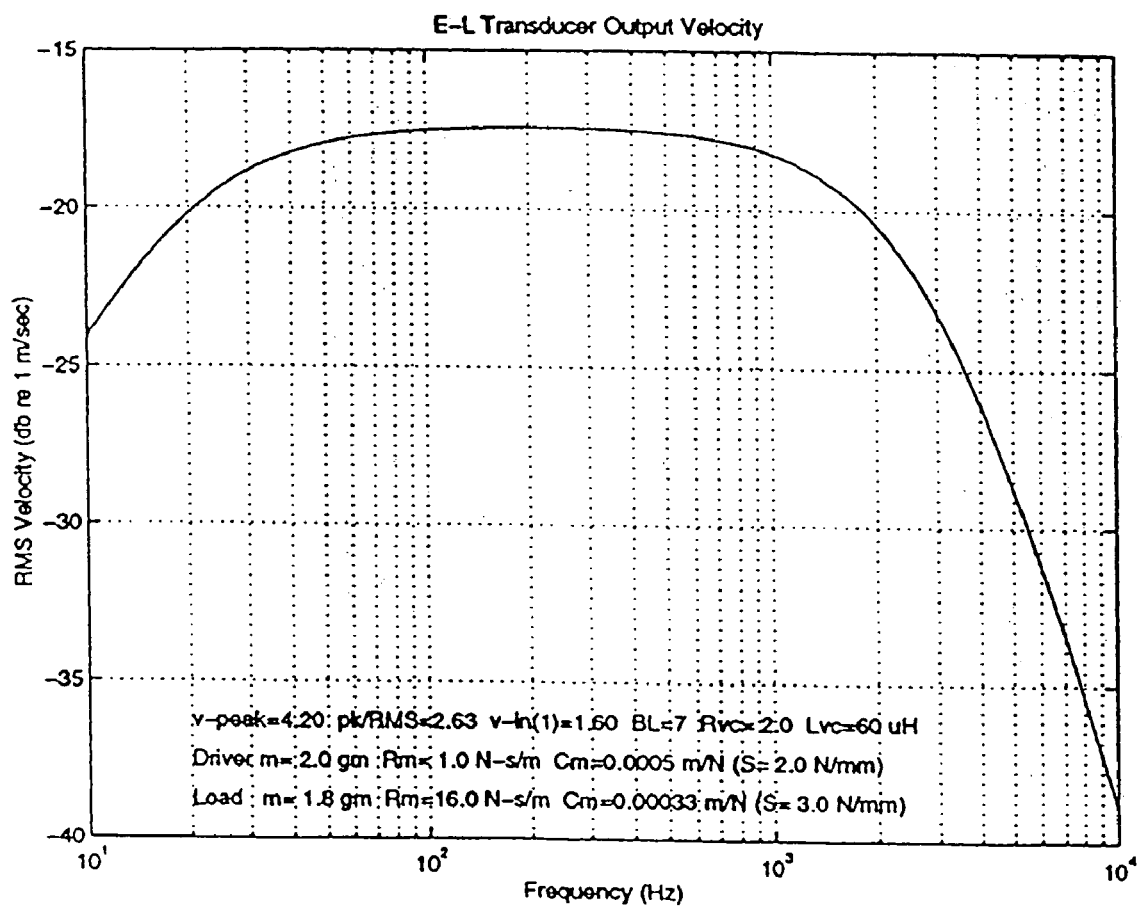
FIG. 8 is a plot of the predicted output velocity of the linear transducers of FIGS. 4A and 4B.

FIGS. 7A and 7B show representative plots of the measured real 710 and imaginary 720 parts, respectively, of the measured transfer function for $M_L(j\omega)$. As can be determined from FIGS. 7A and 7B, the first-order series mass-spring-resistance model, i.e., best-fit curves 715 and 725, provides a reasonable fit to the measured values. Based on various test runs, nominal values of Load Mass $m_L$ of 1.8 grams, Mechanical Resistance $R_{mL}$ of 16 N-s/m, and a Spring Constant $S_L$ of 3.0 N/mm are chosen for design values. In the preferred embodiment, the electro-larynx achieves a substantially flat frequency response with a Load Mass in the range of about 1.1 to 1.9 grams, a Mechanical Resistance in the range of about 8 to 19 N-s/m, and a Spring Constant in the range of about 1.5 to 3.0 N/mm. As shown by the electro-larynx linear transducer output velocity plot of FIG. 8, for an electro-larynx having a 4 volt power amplifier 350 experiencing a load in accordance with these values, and a 2.63 Vrms (about 3.7 Vpeak) swept sinusoid excitation input wave, the resulting nominal velocity frequency response is substantially flat (i.e., linear) over the 20–5 KHz range. With a corresponding predicted velocity of about 0.14 m/sec rms speech outputs of about 85 dBA are predicted.

As a result of the linearity of transducer 310, a substantially linear increase in voltage or current results in a proportional increase in output velocity or acceleration of coupler disk 320. Therefore, the linear transducer has an output coupler disk vibration velocity that is proportional to the input voltage of the shaker. Also, the output wave shape corresponding to the vibration of the coupler disk replicates the input voltage wave shape over the bandwidth of the device. Because the linear transducer has a great deal of responsiveness over a broad spectrum, the attributes of the input glottal source wave are preserved over a similarly broad spectrum. Therefore, it is preferred that the input wave be electronically synthesized to be rich in content, such synthesis allows for a high degree of control over the attributes of the resulting speech, such as spectral shape and tonal quality.

As mentioned previously, it is desirable to set up a sound wave in the pharynx which closely approximates a normal glottal excitation. In normal situations (i.e., with a non-laryngectomee), the user modulates the glottal excitation sound waves with the vocal tract to produce speech output at the lips. Similarly, with the present invention the user modulates the sound waves transduced into the pharynx and originated by the electro-larynx with the vocal tract to produce speech output at the lips. Accordingly, it is important that the generated waveform have a harmonic structure similar to that of normal speech. Therefore, rather than use a waveform model defined over a single cycle and repeated, wherein all harmonics are in lock step, the improved waveform generator of the present invention generates waves having a harmonic structure where the overtones drift in frequency relative to the fundamental, similar to an actual glottal source waveform. Such a harmonic structure allows for the production of a more natural sound, substantially void of the metallic and machine-like sound realized when the harmonics are in lock step.

Figure 9:
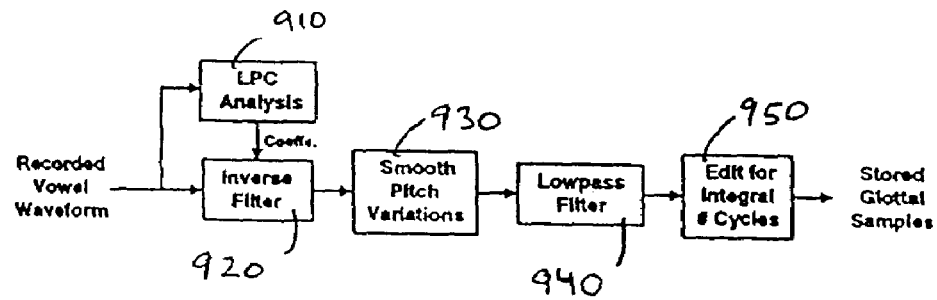
FIG. 9 is a flow diagram depicting the process used to transform voice data into glottal samples for use in the waveform generator of FIG. 3.

In the preferred embodiment, the natural harmonic structure and attributes of normal speech are obtained by synthesizing glottal source waves from glottal sample data that is derived from recorded normal speech. To arrive at the glottal sample data, actual speech is recorded and inverse filtered. This process preserves the harmonic structure, pitch, and amplitude of the recorded voice data. FIG. 9 shows a flow diagram 900 of the preferred process used to transform voice data (in this case recorded voice data) into glottal samples. A held vowel sound is recorded for several seconds and is subsequently Linear Predictive Coding (LPC)—analyzed 910 using a high order filter (e.g., a filter where N=41). This data is then inverse filtered 920 using a time-varying Finite Impulse Response (FIR) filter to obtain a whitened residual. Pitch variations are then smoothed 930 through interpolation and a low pass filter (e.g., 12 dB/octave) is applied. The resulting signal is then edited for an integral number of cycles, and the required glottal samples are stored in a table as digital data and thereby become part of the waveform generator 360. In the preferred embodiment the glottal samples are at least 2 seconds in duration. As this duration is decreased, the periodicity of the table length becomes increasingly and undesirably noticeable. In another embodiment, typical glottal source waveforms are modeled, using a rule-based approach, to represent the relationships between amplitudes and harmonics.

Figure 10A:
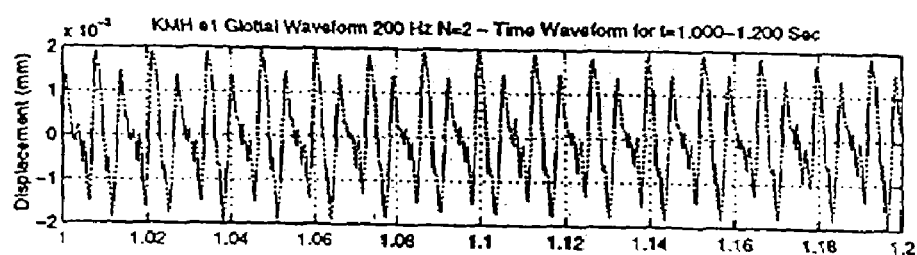
FIGS. 10A, 10B and 10C are plots of the Displacement, Velocity, and Acceleration, respectively, of a glottal waveform produced by the electro-larynx of FIG. 3.
Figure 10B:
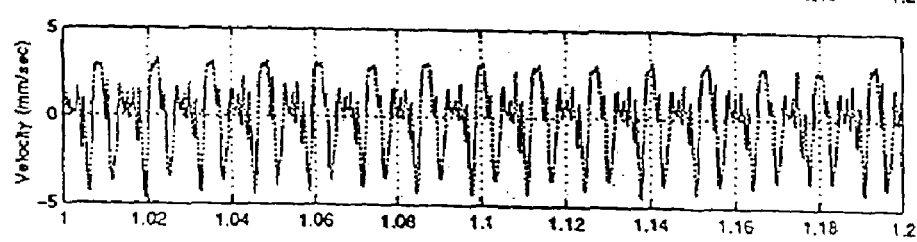
Figure 10C:
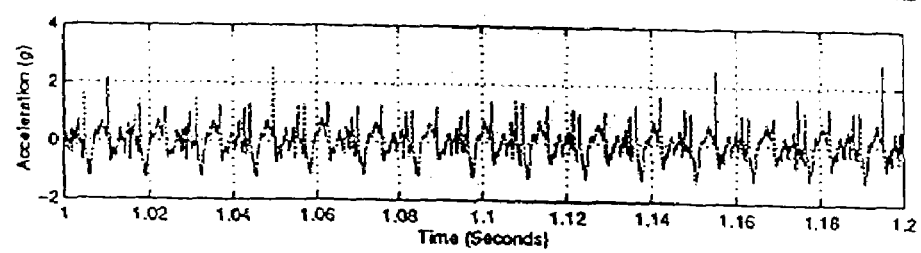

An example of the results of process 900 is shown in FIGS. 10A, 10B, and 10C. FIG. 10A plots the displacement, or amplitude, of the waveform for a 1.000 to 1.200 second time interval. For this same interval, FIG. 10B plots the velocity and FIG. 10C plots the acceleration of the glottal source waveform. As these figures show, there is considerable irregularity from cycle to cycle, unlike the regular waveforms produced by waveform generators having waves defined over a single cycle. As a result of this more "normal" glottal source waveform, when waveform generator source waves are applied to the linear transducer, the metallic machine-like qualities present in single cycle waveform based source waves are absent, and the user's speech retains many of its natural qualities.

Figure 11:
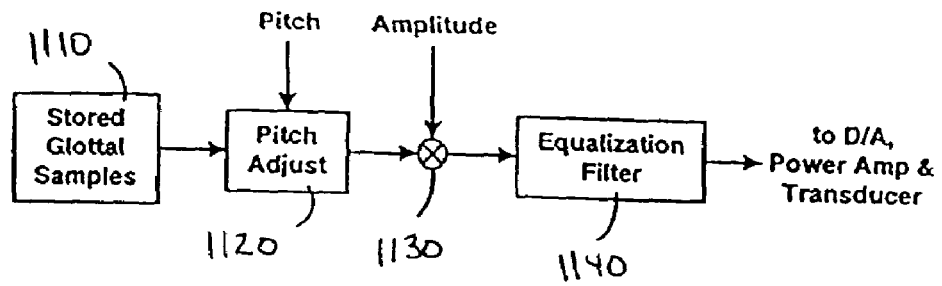
FIG. 11 is a block diagram of the waveform generator of FIG. 3.

A block diagram of the preferred embodiment of the improved waveform generator 360 is shown in FIG. 11. Waveform generator 360 includes a table stored in electronic memory of digital glottal sample data 1110, which is used as the basis for the generated waveform. These base digital glottal samples incorporate the spectral characteristics and harmonic structure of the 220 recorded voice data from which it was derived. A glottal source wave is generated from this data and passed to a pitch adjuster 1120. The pitch adjuster allows manipulation of the pitch of glottal source waveform to accommodate desired speech variations by the user. The resulting wave is passed to multiplier 1130, which allows for user manipulation of the amplitude of the waveform. Pitch and amplitude manipulations are accomplished as a function of user input (via waveform generator terminals 365 of FIG. 3). Such input may be via a user control (e.g., a button) located on housing 330 (also see FIG. 3) or perhaps by biofeedback from the user's laryngeal nerve. Equalization filter 1140 compensates for any high end roll-off in the frequency response of the resulting digital glottal source wave by adding high frequency energy as needed. As an example, to achieve a substantially flat output frequency response spectrum over a bandwidth of about 20–5 KHz, equalization filter 1140 may be required to bolster the frequency response, to some degree, above about 1 KHz, according to known digital signal processing techniques. The equalization filter also smoothes any distortions in the glottal source waveform that may have been caused by the transfer function and process used to obtain the glottal source sample data. The resulting digital glottal source wave is then passed through a digital-to-analog (D/A) converter (not shown). The resulting analog glottal source wave is then passed to power amplifier 350 and is then passed to the linear transducer, as described with respect to FIG. 3.

The inverse filtering approach used to obtain glottal sample data and the digital waveform synthesis of the waveform generator yields potential intangible benefits to users of the improved electro-larynx. For example, if the user had a voice recording taken before the laryngectomee operation (hopefully, well in advance of the affects of the disease on the user's voice), the electro-larynx could be customized to that voice by using the user's own voice recording (including harmonic structure, pitch, and amplitude) to generate the glottal source data. The user therefore could maintain some degree of individuality in the voice and hence reduce some of the hardship currently endured. Alternatively, the voice of a close relative might be adapted to the user, or the user might select a voice from a catalog of voices.

The invention may be embodied in other specific forms without departing from the spirit or central characteristics thereof. For example, a linear transducer and improved waveform generator may be used with other forms of assisted speech devices, such as artificial larynx devices implanted within the user. In other embodiments, either the linear transducer or improved waveform generator may be used with complementary prior art components to achieve an improved electro-larynx. Although, it is preferred that the linear transducer and improved waveform generator are used together. The present embodiments are therefore to be considered in all respects as illustrative and not restrictive, the scope of the invention being indicated by appending claims rather than by the foregoing description, and all changes that come within the meaning and range of equivalency of the claims are therefore intended to be embraced therein.

What is claimed is:

1. An electro-larynx comprising:
   A. a waveform generator configured to selectively generate an input signal characterized by a frequency spectrum;
   B. a linear transducer having a throat engagement portion, said linear transducer configured to receive and transform said input signal into a corresponding output vibration of said throat engagement portion characterized by a frequency spectrum, said output vibration being a substantially linear function of said input signal whereby the frequency spectrum of said vibration matches said frequency spectrum of said input signal; and
   C. a power source.

2. An electro-larynx according to claim 1, wherein the linear transducer includes:
   a. an armature assembly, which receives said input signal and vibrates as a function thereof;
   b. a suspension assembly coupled to said armature assembly; and
   c. a coupler disk, as said engagement portion, coupled to said suspension assembly, wherein a vibration in said armature assembly causes a corresponding vibration of said coupler disk.

3. An electro-larynx according to claim 2 wherein the suspension assembly is a flexible planar membrane.

4. An electro-larynx according to claim 2 wherein the suspension assembly is a mechanical spring.

5. An electro-larynx according to claim 2 wherein the armature assembly is substantially disposed within a cylindrical motor assembly that defines an internal void region along a central axis and having an radial magnetic field maintained within said internal void region, and wherein said armature assembly includes:
   a. a bobbin coupled to said suspension assembly and disposed within said internal void region and along said central axis; and
   b. a wire coil wrapped around said bobbin and within said magnetic field;
whereby when said input signal is applied to said wire coil a corresponding vibration of said bobbin is experienced.

6. An electro-larynx according to claim 2 wherein the armature assembly includes a piezo-electric actuator coupled to said engagement portion, wherein an input signal delivered to said piezo-electric actuator causes a corresponding linear vibration of said engagement portion.

7. An electro-larynx according to claim 2 wherein the armature assembly includes a magneto-resistive element coupled to said engagement portion, wherein an input signal delivered to said magneto-resistive element causes a corresponding linear vibration of said engagement portion.

8. An electro-larynx according to claim 1 wherein the linear transducer has a substantially flat frequency response over a range of about 20 to 2 KHz.

9. An electro-larynx according to claim 1 wherein said input signal generated by said waveform generator has a harmonic structure corresponding to a normal glottal excitation, defined over multiple cycles.

10. An electro-larynx according to claim 1 wherein the waveform generator includes:
    a. glottal sample data stored in an electronic memory;
    b. a pitch adjuster, configured to add pitch information to said glottal sample data;
    c. a multiplier, configured to add amplitude information to said glottal sample data;
    d. an equalization filter for generating from said glottal sample data, pitch information, and amplitude information a base digital input signal having a predetermined frequency response; and
    e. a digital to analog converter, configured to transform said base digital input signal into said input signal.

11. An electro-larynx according to claim 10 wherein the glottal sample data is obtained by inverse filtering and digitally sampling voice data.

12. A linear transducer, for use in an electro-larynx having a waveform generator that produces an input signal and a power source, said linear transducer comprising:
    A. an armature assembly, which receives said input signal characterized by a frequency spectrum and vibrates as a function thereof;
    B. a suspension assembly coupled to said armature assembly; and
    C. a coupler disk, coupled to said suspension assembly, wherein a vibration in said armature assembly causes a corresponding vibration of said coupler disk characterized by a frequency spectrum according to a linear function of said input signal, whereby the frequency spectrum of said vibration matches said frequency spectrum of said input signal.

13. A linear transducer according to claim 12 wherein the suspension assembly is a flexible planar membrane.

14. A linear transducer according to claim 12 wherein the suspension assembly is a mechanical spring.

15. A linear transducer according to claim 12 wherein the armature assembly is substantially disposed within a cylindrical motor assembly that defines an internal void region along a central axis and having a magnetic field maintained with said internal void region, and wherein said armature assembly includes:
    a. a bobbin coupled to said suspension assembly and disposed within said internal void region and along said central axis; and
    b. a wire coil wrapped around said bobbin and within said magnetic field;
whereby when said input signal is applied to said wire coil a corresponding vibration of said bobbin is experienced.

16. A linear transducer according to claim 12 wherein the armature assembly includes a piezo-electric actuator coupled to said coupler disk, wherein an input signal delivered to said piezo-electric actuator causes a corresponding linear vibration of said coupler disk.

17. A linear transducer according to claim 12 wherein the armature assembly includes a magneto-resistive element coupled to said coupler disk, wherein an input signal delivered to said magneto-resistive element causes a corresponding linear vibration of said coupler disk.

18. A linear transducer according to claim 12 wherein the linear transducer has a substantially flat frequency response over a range of about 20 to 2 KHz.

19. An electro-larynx comprising:
a waveform generator comprising:
  A. glottal sample data stored in an electronic memory, wherein said glottal sample data is defined over multiple cycles;
  B. a pitch adjuster, configured to add pitch information to said glottal sample data;
  C. a mixer, configured to add amplitude information to said glottal sample data;
  D. an equalization filter for generating from said glottal sample data, pitch information, and amplitude information, a base digital input signal having a predetermined frequency response; and
  E. a digital to analog converter, configured to transform said base digital input signal into an input signal, characterized by a frequency spectrum;
    a linear transducer configured to receive and transform said input signal into a corresponding output vibration of a throat engagement portion characterized by a frequency spectrum, said output vibration being a substantially linear function of said input signal whereby the frequency spectrum of said vibration matches said frequency spectrum of said input signal.

20. A waveform generator according to claim 19 wherein the glottal sample data is obtained by inverse filtering and digitally sampling voice data.

21. A waveform generator according to claim 19 wherein the glottal sample data is derived from a mathematical model which preserves the harmonic qualities of the voice data.

22. An electro-larynx comprising:
  A. a waveform generator configured to selectively generate an input signal characterized by a frequency spectrum, wherein said input signal has a harmonic structure corresponding to a normal glottal excitation, defined over multiple cycles;
  B. a linear transducer having a throat engagement portion, said transducer configured to receive and transform said input signal into a corresponding output vibration of said throat engagement portion characterized by a frequency spectrum said output vibration being a substantially linear function of said input signal whereby the frequency spectrum of said vibration matches said frequency spectrum of said input signal; and
  C. a power source.

23. An electro-larynx according to claim 22 wherein the waveform generator includes:
  a. glottal sample data stored in an electronic memory;
  b. a pitch adjuster, configured to add pitch information to said glottal sample data;
  c. a multiplier, configured to add amplitude information to said glottal sample data;
  d. an equalization filter for generating from said glottal sample data, pitch information, and amplitude information a base digital input signal having a predetermined frequency response; and
  e. a digital to analog converter, configured to transform said base digital input signal into said input signal.

24. An electro-larynx according to claim 23 wherein the glottal sample data is obtained by inverse filtering and digitally sampling voice data.

25. An electro-larynx according to claim 23 wherein the glottal sample data is derived from a mathematical model which preserves the harmonic qualities of the voice data.

* * * * *